(12) United States Patent
Meng et al.

(10) Patent No.: US 9,796,728 B2
(45) Date of Patent: Oct. 24, 2017

(54) CYCLIC CARBONATE MONOMER CONTAINING DOUBLE-SULFUR FIVE-MEMBERED RING FUNCTIONAL GROUP, AND PREPARATION METHOD THEREOF

(71) Applicant: BrightGene Bio-Medical Technology Co., Ltd., Jiangsu (CN)

(72) Inventors: Fenghua Meng, Jiangsu (CN); Yan Zou, Jiangsu (CN); Zhiyuan Zhong, Jiangsu (CN); Jiandong Yuan, Jiangsu (CN)

(73) Assignee: Brightgene Bio-Medical Technology Co., Ltd., Jiangsu (CN)

( * ) Notice: Subject to any disclaimer, the term of this patent is extended or adjusted under 35 U.S.C. 154(b) by 0 days.

(21) Appl. No.: 15/314,207

(22) PCT Filed: May 27, 2015

(86) PCT No.: PCT/CN2015/079998
§ 371 (c)(1),
(2) Date: Nov. 28, 2016

(87) PCT Pub. No.: WO2015/180655
PCT Pub. Date: Dec. 3, 2015

(65) Prior Publication Data
US 2017/0174701 A1    Jun. 22, 2017

(30) Foreign Application Priority Data
May 28, 2014 (CN) .......................... 2014 1 0231697

(51) Int. Cl.
| | | |
|---|---|---|
| C07D 495/10 | (2006.01) |
| A61K 47/34 | (2017.01) |
| A61K 9/51 | (2006.01) |
| C08G 64/02 | (2006.01) |
| C08G 64/30 | (2006.01) |
| C08G 64/18 | (2006.01) |
| C08G 64/42 | (2006.01) |

(52) U.S. Cl.
CPC .......... *C07D 495/10* (2013.01); *A61K 9/5153* (2013.01); *A61K 47/34* (2013.01); *C08G 64/025* (2013.01); *C08G 64/183* (2013.01); *C08G 64/305* (2013.01); *C08G 64/42* (2013.01)

(58) Field of Classification Search
CPC .................................................... C07D 495/10
USPC ...................................................... 549/33, 60
See application file for complete search history.

(56) References Cited

FOREIGN PATENT DOCUMENTS

| | | |
|---|---|---|
| CN | 101633654 | 1/2010 |
| CN | 102657873 | 9/2012 |
| CN | 104004001 | 8/2014 |
| CN | 104031248 | 9/2014 |
| JP | 2001131170 | 5/2000 |
| WO | 2013/004296 | 1/2013 |

OTHER PUBLICATIONS

International Search Report for PCT/CN2015/0799898 issued Sep. 8, 2015.

*Primary Examiner* — Taofiq A Solola
(74) *Attorney, Agent, or Firm* — Fish & Richardson P.C.

(57) ABSTRACT

Disclosed are a cyclic carbonate monomer containing a double-sulfur five-membered ring functional group, and preparation method thereof. The cyclic carbonate monomer can be simply and efficiently synthesized without protection and deprotection processes. The cyclic carbonate monomer of the present invention can be utilized to obtain polycarbonate having a controllable molecular weight and molecular weight distribution via ring opening polymerization, and has biodegradability and reduction-sensitive reversible crosslinking properties. The present invention can be used in a carrier having controllably released drug, a biological tissue scaffold or a biochip.

8 Claims, 5 Drawing Sheets

CYCLIC CARBONATE MONOMER CONTAINING DOUBLE-SULFUR FIVE-MEMBERED RING FUNCTIONAL GROUP, AND PREPARATION METHOD THEREOF

TECHNICAL FIELD

The present disclosure relates to a cyclic carbonate monomer, and the preparation and application of a cyclic carbonate monomer containing double-sulfur five-membered ring functional group.

BACKGROUND ART

The cyclic carbonate monomers have unique properties. For example, they can be simply synthesized into products with high yield and high purity; and they can be initiated through small molecules or macromolecules to obtain bio-degradable polycarbonate. The polymers of the cyclic carbonate monomers have outstanding performance. For example, they generally have favorable biocompatibility, and can be degraded in vivo; the degradation products can be absorbed in human body, or be excreted through normal physiological pathways. Similar with the aliphatic polyesters, they are widely used in various areas of biomedicine, e.g. surgical sutures, orthopedic fixation devices, scaffold materials for biological tissue engineering, carriers for controlled drug release, etc. Among these, the synthetic biodegradable polymers received much attention, since they have low immunogenicity, and their performances like degradation performance and mechanical performance can be conveniently controlled. The commonly used bio-degradable polymers are obtained through ring-opening polymerization of cyclic carbonate monomers like cyclic trimethylene carbonate (TMC), or cyclic ester monomers like glycolide (GA), lactide (LA), caprolactone (CL), etc. The bio-degradable polymers have been approved by the U.S. Food and Drug Administration (FDA).

Technical Problems

However, the cyclic carbonate or cyclic ester monomers in prior art, e.g. TMC, GA, LA, CL and the like have simple structure, and lack functional groups which can be modified. Therefore the polymers prepared therefrom are usually difficult for post-modification, thus the medical requirements are hardly satisfied. For example, the drug carriers or the surface modified coatings based on these polymers of these conventional carbonate monomers have fatal weakness of poor stability. Improving their stability in vivo has become an urgent problem to be solved.

In addition, in prior art, during the process of preparation and/or ring-opening polymerization of cyclic carbonate monomers, since there are reactive groups in the structure, in most cases the steps of protection and deprotection are required, which make the preparation process complicated.

SUMMARY OF THE DISCLOSURE

Solution to the Problem

The present disclosure is intended to provide a cyclic carbonate monomer containing double-sulfur five-membered ring functional group.

For this purpose, the embodiment of the present disclosure includes: a cyclic carbonate monomer containing double-sulfur five-membered ring functional group, represented by the following formula:

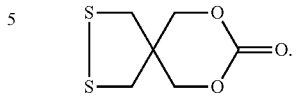

The method for preparing the aforesaid cyclic carbonate monomer includes the following steps: in a polar solvent, reacting dibromoneopentyl glycol with sodium hydrosulfide monohydrate to obtain Compound A; then oxidizing Compound A in air to obtain Compound B; finally, in nitrogen atmosphere and cyclic ether-based solvents, reacting Compound B with ethyl chloroformate to obtain the cyclic carbonate monomer containing double-sulfur five-membered ring functional group.

In the aforesaid embodiment, the molar ratio of dibromoneopentyl glycol to sodium hydrosulfide monohydrate is (2.5~10):1; and the molar ratio of Compound B to ethyl chloroformate is 1:(2~4).

In a preferred embodiment, the method for preparing the aforesaid cyclic carbonate monomer containing double-sulfur five-membered ring functional group comprises:

(1) Dissolving sodium hydrosulfide monohydrate in a polar solvent; slowly adding dibromoneopentyl glycol dropwise with a pressure-equalizing dropping funnel; maintaining the reaction temperature at 50° C. for 48 hours to obtain Compound A:

said Compound A is represented by the following formula:

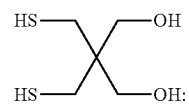

(2) Oxidizing Compound A in air to obtain Compound B, said Compound B is represented by the following formula:

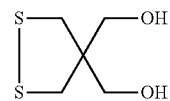

(3) In nitrogen atmosphere, dissolving Compound B and ethyl chloroformate into a cyclic ether-based solvent, then slowing adding triethylamine dropwise with a pressure-equalizing dropping funnel; controlling the reaction temperature with ice water bath for 4 hours to obtain cyclic carbonate monomer containing double-sulfur five-membered ring functional group, said cyclic carbonate monomer is represented by the following formula:

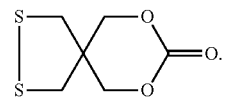

In a preferred embodiment, said polar solvent is N,N-dimethylformide (DMF); said ether-based solvent is tetrahydrofuran.

In a preferred embodiment, Compound A is firstly dissolved in an ether-based solvent, then oxidized in air to obtain Compound B; thus the oxidation rate of Compound A is increased. The ether-based solvent can be tetrahydrofuran, 1,4-dioxane. In order to simplify the reaction process and simplify the reaction condition, the solvent for dissolving Compound A in step (2) is consistent with the solvent for dissolving Compound B in step (3).

In a preferred embodiment, purification treatment is performed after completing step (1) and step (3); in detail:

(1) Purification of Compound A: when the reaction is completed, the resulted mixture is subjected to distillation under reduced pressure for removing the solvent, and the obtained residue is diluted with distilled water, then extracted with ethyl acetate; finally the organic phase is evaporated with rotary evaporator, and the yellow and viscous Compound A is obtained;

(2) Purification of the cyclic carbonate monomer containing double-sulfur five-membered ring functional group: filtration is performed after the reaction is completed; the filtrate is concentrated with a rotary evaporator, then recrystallized with ethyl ether to obtain a yellow crystal, which is the cyclic carbonate monomer containing double-sulfur five-membered ring functional group.

The aforesaid distillation under reduced pressure, extraction, evaporation with rotary evaporator, concentration with rotary evaporator and recrystallization all belong to prior art. Those skilled in the art can select the method as desired. In the present disclosure, it is preferable that when purifying the Compound A, extraction with ethyl acetate is performed four times,; when purifying the cyclic carbonate, recrystallization with ethyl ether is performed 3~5 times.

The aforesaid process for preparing the cyclic carbonate monomer containing double-sulfur five-membered ring functional group is illustrated as follows:

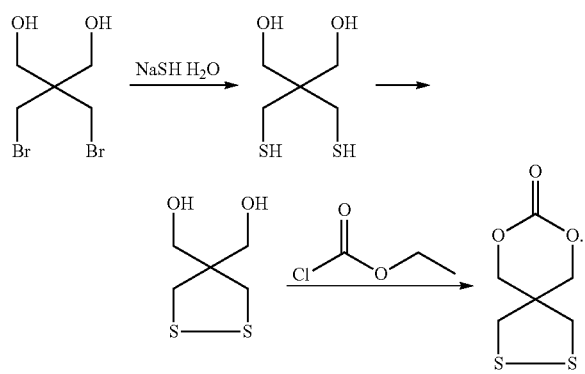

The aforesaid cyclic carbonate monomer containing double-sulfur five-membered ring functional group can be subjected to ring-opening polymerization to obtain a polycarbonate with side chain containing double-sulfur five-membered ring. Since the double-sulfur five-membered ring group does not affect the ring-opening polymerization, protection and deprotection processes are not required. For example, in dichloromethane, using polyethylene glycol as initiator and using zinc bis[bis(trimethylsilyl)amide] as catalyst, the aforesaid cyclic carbonate monomer forms a block polymer through ring-opening polymerization, where the reaction formula is shown below:

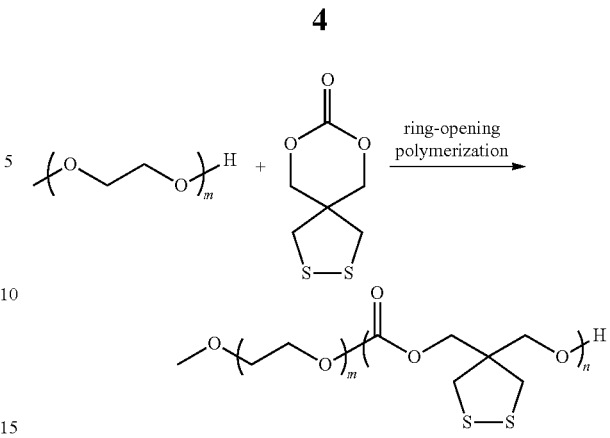

the cyclic carbonate monomer above may further have ring-opening copolymerization with other cyclic ester, cyclic carbonate monomers, to prepare random and block copolymers; said other cyclic carbonates include cyclic trimethylene carbonate (TMC), said other cyclic ester monomers include caprolactone (ε-CL), lactide (LA) or glycolide (GA).

The functional carbonate with side chain containing double-sulfur five-membered ring may form stable chemical crosslink under catalysis by catalytic amount of reducer like dithiothreitol or glutathione, but it may de-crosslink rapidly in the intracellular reducing environment. Therefore the functional carbonate with side chain containing double-sulfur five-membered ring has excellent practical value, for example, it may be used for preparing drug carriers that are stable in circulation which may rapidly release the drugs in the target cells.

Advantageous Effects of the Technology

Due to the practice of the aforesaid embodiment, the present disclosure has the following advantages over prior art:

1. The present disclosure for the first time discloses a cyclic carbonate monomer containing double-sulfur five-membered ring functional group, which can be conveniently prepared in high efficiency with only two pots (three steps), without the protection and deprotection processes in prior art.

2. The present disclosure discloses a cyclic carbonate monomer containing double-sulfur five-membered ring functional group, with which a functional polycarbonate with side chain containing double-sulfur five-membered ring can be obtained through ring-opening polymerization, where the protection and deprotection processes in prior art are not required, since the double-sulfur five-membered group does not affect the ring-opening polymerization of the cyclic carbonate monomer.

3. The preparation of the cyclic carbonate monomer disclosed in the present disclosure is simple. Through the convenient ring-opening polymerization of the cyclic carbonate monomers, a carbonate polymer characterized in sensitivity to reducing and reversible crosslink is obtained; the polymer could be further self-assembled thus being used in controlled drug release system, tissue engineering and biological chips, showing advantageous application value in the area of biomaterials.

DESCRIPTION OF THE EMBODIMENTS

The present disclosure will be further described with reference to the examples and drawings.

EXAMPLE 1

Synthesis of Cyclic Carbonate Monomer Containing Double-Sulfur Five-Membered Ring Functional Group (CDC)

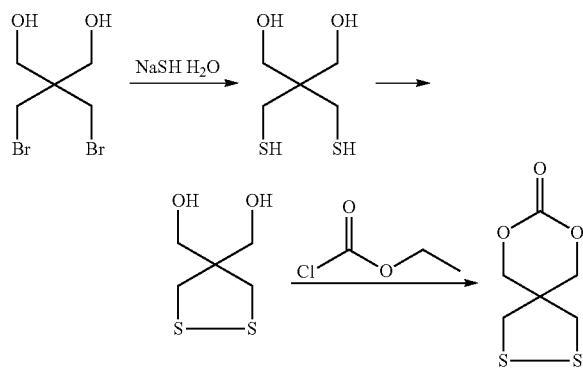

1. Sodium hydrosulfide monohydrate (28.25 g, 381.7 mmol) was dissolved in 400 mL of N,N-dimethylformide (DMF), heated at 50° C. till completely dissolved, and dibromoneopentyl glycol (20 g, 76.4 mmol) was added dropwise thereto. The reaction was allowed to proceed for 48 h. The reaction mixture was distilled under reduced pressure to remove the solvent DMF, and then diluted with 200 mL of distilled water, extracted four times with 250 mL of ethyl acetate. Finally the organic phase was evaporated with rotary evaporator, and a yellow viscous Compound A was obtained with yield of 70%.

2. The Compound A dissolved in 400 mL of tetrahydrofuran (THF) was placed in air for 24 h. The intramolecular sulfhydryl groups were oxidized into sulfur-sulfur bonds, thus the Compound B was obtained, with yield of >98%.

3. Under the protection of nitrogen, the Compound B (11.7 g, 70.5 mmol) was dissolved in dried THF (150 mL), stirred till completely dissolved, then cooled to 0° C. Ethyl chloroformate (15.65 mL, 119.8 mmol) was added. Then $Et_3N$ (22.83 mL, 120.0 mmol) was added dropwise. After finishing the addition, the system was allowed to further react in ice water bath for 4 h. When the reaction was completed, the $Et_3N.HCl$ produced was removed through filtration. The filtrate was concentrated with rotary evaporator. Finally, recrystallization was performed several times using ethyl ether, to obtain a yellow crystal, i.e. the cyclic carbonate monomer containing double-sulfur five-membered ring functional group (CDC), with yield of 64%.

Figure 1:
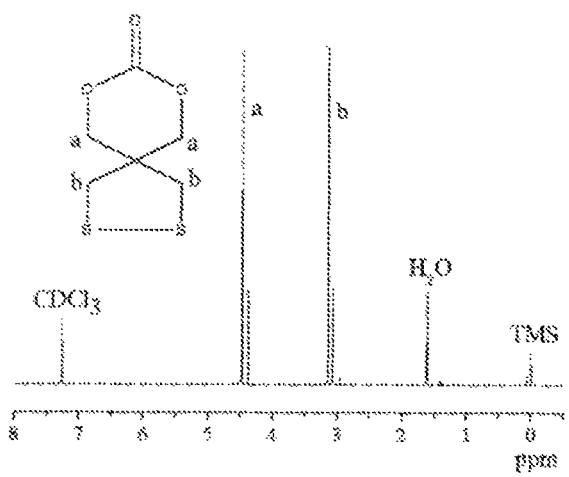
FIG. 1 is an NMR spectrum of the cyclic carbonate monomer containing double-sulfur five-membered ring functional group in Example 1.
Figure 2:
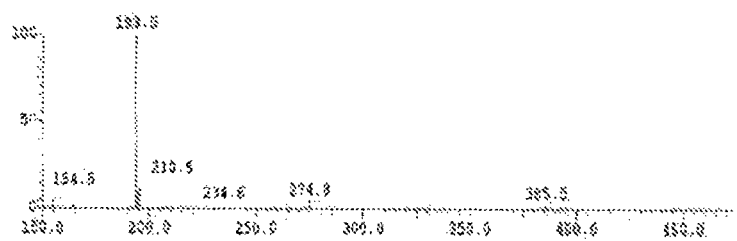
FIG. 2 is a mass spectrum of the cyclic carbonate monomer containing double-sulfur five-membered ring functional group in Example 1.
Figure 3:
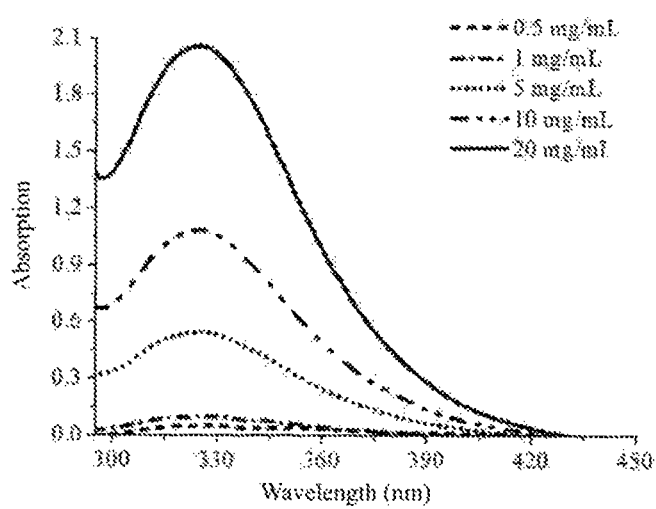
FIG. 3 is an ultraviolet absorption spectrum of the cyclic carbonate monomer containing double-sulfur five-membered ring functional group in Example 1.

FIG. 1 is an NMR spectrum of the above product CDC, $^1$H NMR (400 MHz, $CDCl_3$): δ3.14 (s, 4H), 4.51 (s, 4H). Elementary analysis: C: 41.8%, H: 4.20%, O: 24.3% (In theory: C: 41.67%, H: 4.17%, O:25%, S: 33.3%). Mass spectrometry analysis of the CDC monomer: MS: 192.5 (theoretical molecular weight: 192), see FIG. 2. FIG. 3 shows the ultraviolet spectra of the solutions of aforesaid product monomer CDC in tetrahydrofuran with various concentrations. The sulfur-sulfur five-membered ring in the monomer has absorption at 330 nm, while the absorption intensity increases along with the increase of monomer concentration.

EXAMPLE 2

Synthesis of Cyclic Carbonate Monomer Containing Double-Sulfur Five-Membered Ring Functional Group (CDC)

1. Sodium hydrosulfide monohydrate (28.25 g, 381.7 mmol) was dissolved in 400 mL of dimethyl sulfoxide (DMSO), heated at 40° C. till completely dissolved. Dibromoneopentyl glycol (20 g, 76.4 mmol) was added dropwise. The reaction was allowed to proceed for 48 h. The reaction mixture was distilled under reduced pressure to remove the solvent DMSO, and then diluted with 200 mL of distilled water, extracted four times with 250 mL of ethyl acetate. Finally the organic phase was evaporated with rotary evaporator, and a yellow viscous Compound A was obtained with yield of 42%.

2. The Compound A dissolved in 400 mL of 1,4-dioxane was placed in air for 24 h. The intramolecular sulfhydryl groups were oxidized into sulfur-sulfur bonds, thus the Compound B was obtained, with yield of >98%.

3. Under the protection of nitrogen, the Compound B (11.7 g, 70.5 mmol) was dissolved in dried 1,4-dioxane (150 mL), stirred till completely dissolved, then cooled to 0° C. Ethyl chloroformate (15.65 mL, 119.8 mmol) was added. Then $Et_3N$ (22.83 mL, 120.0 mmol) was added dropwise. After finishing the dropwise addition, the system was allowed to further react in ice water bath for 4 h. When the reaction was completed, the $Et_3N.HCl$ produced was removed through filtration. The filtrate was concentrated with rotary evaporator. Finally, recrystallization was performed several times using ethyl ether, to obtain a yellow crystal, i.e. the cyclic carbonate monomer containing double-sulfur five-membered ring functional group (CDC), with yield of 32%.

EXAMPLE 3

Synthesis of Diblock Polymer PEG5k-b-PCDC2.8k

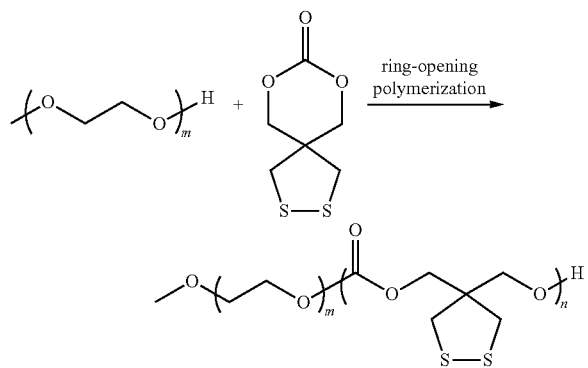

In the formula, m=114, n=14.6.

In nitrogen environment, 0.3 g (1.56 mmol) of cyclic carbonate monomer containing double-sulfur five-membered ring functional group (CDC) and 2 mL of dichloromethane were added into a sealed reactor. Then 0.5 g (0.1 mmol) of polyethylene glycol with molecular weight of 5,000, and 1 mL solution of catalyst zinc bis[bis(trimethylsilyl)amide] in dichloromethane (0.1 mmol) were added. Then the reactor was tightly sealed, transferred out from the glove cabinet, put into oil bath at 40° C., The reaction was allowed to proceed for 1 day, and terminated by glacial acetic acid, precipitated in ice-cold ethyl ether. Finally, after filtration and vacuum drying, the product cyclic carbonate polymer PEG5k-h-PCDC2.8k was obtained.

Figure 4:
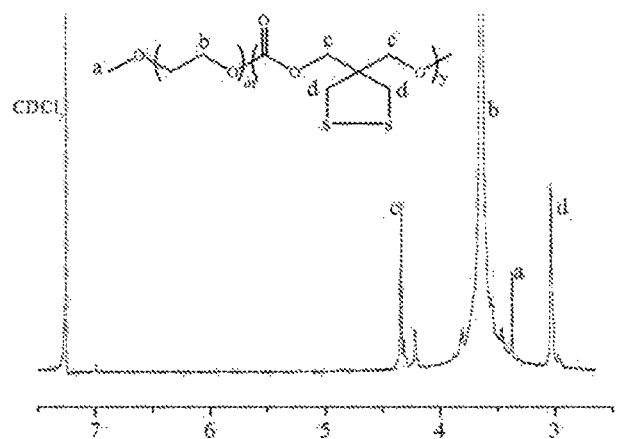
FIG. 4 is an NMR spectrum of the block copolymer PEG5k-b-PCDC2.8k in Example 3.

FIG. 4 is an NMR spectrum of the aforesaid cyclic carbonate polymer: $^1$H NMR (400 MHz, CDCl$_3$): 3.08 (s, —CCH$_2$), 3.30 (m, —OCH$_3$), 4.05 (s, —CH$_2$OCOCHCH$_2$—), 4.07 (s, —OCH$_2$CCH$_2$O—), 4.31 (m, —CCH$_2$).

EXAMPLE 4

Synthesis of Diblock Polymer PEG5k-P(CDC2.5k-co-CL3.9k)

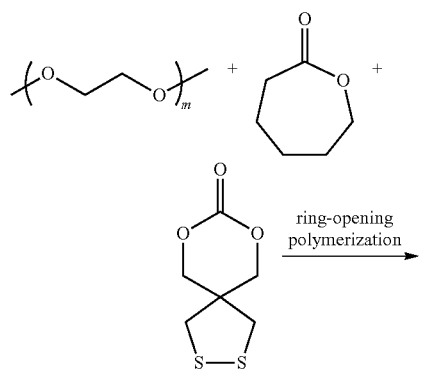

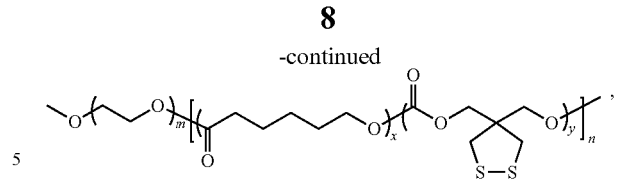

in the formula, m=114, x=21.9, y=13.0, n=34.9.

In nitrogen environment, 0.28 g (1.46 mmol) of CDC monomer and 0.4 g (3.51 mmol) of caprolactone (E-CL) were dissolved in 3 mL of dichloromethane, and added into a sealed reactor. Then 0.5 g (0.1 mmol) of polyethylene glycol with molecular weight of 5,000, and 1 mL solution of catalyst zinc bis[bis(trimethylsilyl)amide] in dichloromethane (0.1 mol/L) were added. Then the reactor was tightly sealed, transferred out from the glove cabinet, put into oil bath at 40° C., The reaction was allowed to proceed for 1 day, and terminated by glacial acetic acid, precipitated in ice-cold ethyl ether. Finally, after filtration and vacuum drying, the product cyclic carbonate polymer PEG5k-P(CDC2.5k-co-CL3.9k) was obtained.

Figure 5:
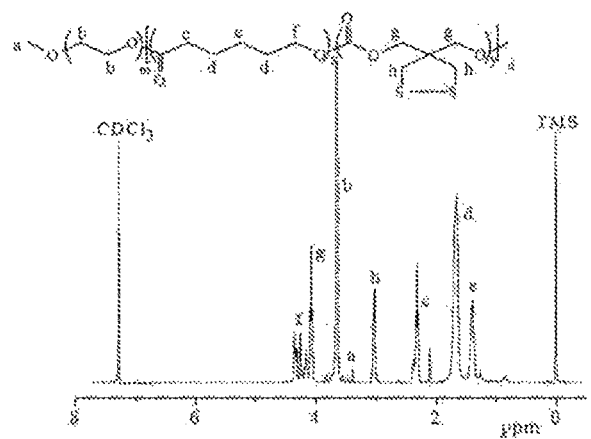
FIG. 5 is an NMR spectrum of the block copolymer PEG5k-P(CDC2.5k-co-CL3.9k) in Example 4.

FIG. 5 is an NMR spectrum of the aforesaid polymer: $^1$H NMR (400 MHz, CDCl$_3$): 1.40 (m, —COCH$_2$CH$_2$CH$_2$CH$_2$CH$_2$—), 1.65 (m, —COCH$_2$CH$_2$CH$_2$CH$_2$CH$_2$—), 2.30 (t, —COCH$_2$CH$_2$CH$_2$CH$_2$CH$_2$—), 3.08 (s, —CCH$_2$), 3.30 (m, —OCH$_3$), 4.03 (t, —COCH$_2$CH$_2$CH$_2$CH$_2$CH$_2$O—), 4.05 (s, —CH$_2$OCOCHCH$_2$—), 4.07 (s, —OCH$_2$CCH$_2$O—), 4.31 (m, —CCH$_2$): molecular weight determined by GPC: 14.0 kDa, molecular weight distribution: 1.56.

EXAMPLE 5

Preparation of Polymer Micelle Nanoparticles PEG5k-h-PCDC2.8k

The polymer micelle nanoparticles were prepared through dialysis. The polymer PEG5k-b-PCDC2.8k was dissolved in N,N-dimethylformide (2 mg/mL), then 200 μL of the solution was taken and added dropwise into 800 μL of phosphate buffer solution (10 mM, pH 7.4, PB), put into a dialysis bag; the dialysis was performed overnight, while the fluid was replaced five times. The medium for dialysis was PB (10 mM, pH 7.4). The finally obtained polymer nanoparticles had concentration of 0.2 mg/mL.

EXAMPLE 6

Crosslink, De-Crosslink and Cytotoxicity of Polymer Nanoparticles PEG5k-b-PCDC2.8k The crosslink of the nanoparticles was performed with addition of catalytic amount of dithiothreitol (DTT). Nitrogen was introduced into the aqueous solution of the polymer nanoparticles for 10 min to remove the air as much as possible. Then 10 μL of dithiothreitol (DTT) dissolved in dd-H$_2$O (0.007 mg, 4.67×10$^{-5}$ mmol, mole number of lipoic acid functional groups: 10%) was added into the nanoparticle solution (1 mL, 0.25 mg/mL, 3.21×10$^{-5}$ mmol) in sealed reactor. The mixture was sealed, stirred at room temperature and allowed to react for 1 day. The measured size of the particles was 150 nm, which was 15% less than the size of the non-crosslinked particles. After 100-fold dilution, there was almost no change in particle size and particle size distribution of the crosslinked nanoparticles. The nanoparticles were stable in physiological condition.

Therefore it can be observed that double sulfur crosslink can improve the stability of the nanoparticles to a considerable extent.

The sulfur-sulfur bond can readily break under the action of reducers like glutathione (GSH). Under the condition of nitrogen protection and at 37° C., the crosslinked nanoparticles were bubbled with nitrogen for 10 min, then GSH was added till its final concentration in the solution of polymer nanoparticles reached 10 mM. The particle size of the crosslinked nanoparticles was broken over time, indicating that the double-sulfur ring in the polymer would break in the presence of large amount of reducing substances. There is also high concentration of reducing substance GSH in the cytoplasm. Therefore, the prepared nano drug carriers are stable in circulation, but can be rapidly dissociate and release the drug once taken by the cells through endocytosis.

The cytotoxicity of the crosslinked micelle nanoparticles was tested with MTT method. The cells used were MCR-7 cell (human breast cancer cell) and Raw 264.7 cell (mouse macrophage). The MCF-7 cells or the Raw 264.7 cells were seeded into 96-well plates at 1×10⁴ cells/mL, 100 μL for each well. The cells were cultured till they adhered to the culture vessels, then for the experimental group, the media containing polymer nanoparticles in various concentrations were added. In addition, the cell-free blank control and medium-free blank wells were assigned. Parallel wells were provided in quadruplicate. After 24 h incubation in the incubator, the 96-well plates were taken out, then 10 μL MTT (5.0 mg/mL) was added. After another 4 h incubation, 150 μL DMSO was added into each well to dissolve the crystal formed. The absorption value (A) at 492 nm was determined with microplate reader. A zero adjustment was performed with the medium-free blank wells. The cell survival rate was calculated.

$$\text{Cell survival rate } (\%) = \frac{A_T}{A_C} \times 100\%$$

Figure 6:
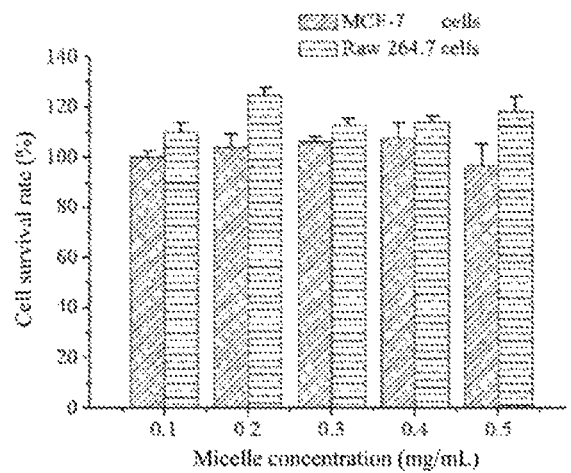
FIG. 6 is a graph showing the toxicity of the crosslinked nanoparticles of polymer PEG5k-h-PCDC2.8k on Raw264.7 and MCF-7 cells in Example 6.

In the formula, $A_T$ was the absorption at 490 nm of the experimental group, and $A_C$ was the absorption at 492 nm of the blank control group. The concentrations of the polymer were 0.1, 0.2, 0.3, 0.4, 0.5 mg/mL respectively. FIG. 6 shows the cytotoxicity result of the nanoparticles. It can be observed from FIG. 6 that, when the concentration of the polymer nanoparticles was increased to 0.5 mg/mL from 0.1 mg/mL, the survival rate of the Raw 264.7 cells and the MCF-7 cells was still higher than 85%, indicating that the PEG5k-b-PCDC2.8k polymer nanoparticles has favorable biocompatibility.

EXAMPLE 7

Drug Carrying, in vitro Release and Cytotoxicity of the Crosslinked Micelle Nanoparticles PEG5k-h-PCDC2.8k Doxorubicin was used as the drug. Since the anticancer drug doxorubicin was a fluorescence sensitive substance, the whole procedure was protected from light. Firstly, the hydrochloride salt of doxorubicin was removed through the following procedure: 1.2 mg (0.002 mmol) doxorubicin was dissolved in 225 μL DMSO, then 0.58 mL triethylamine (m=0.419 mg, 0.004 mmol) was added, stirred for 12 h. The supernatant was sucked off. The concentration of doxorubicin solution in DMSO was 5.0 mg/mL. The nano-polymer nanoparticles PEG5k-b-PCDC2.8k was dissolved in N,N-dimethylformide (DMF). The solution of doxorubicin in DMSO and the solution of polymer nanoparticles PEG5k-b-PCDC2.8k in DMF were thoroughly mixed at predetermined drug to polymer mass ratio. Under agitation, dd-H₂O whose volume was four times of the mixture was slowly added (15 s/d). When the dropwise addition was completed, the mixture was subjected to dialysis with distilled water.

The crosslink of the drug-loaded micelle nanoparticles was also performed according to the crosslink method described in Example 5. The solution of the crosslinked, doxorubicin-loaded polymer nanoparticles (100 μL) was subjected to freeze-drying, and then dissolved in 3.0 mL DMSO, measured by fluorescent spectrophotometer. The encapsulation rate was calculated with reference to the standard curve of doxorubicin.

Drug loading content (DLC) and drug loading efficiency (DLE) were calculated according to the following formula:

Drug loading content (wt. %)=(weight of the drug/weight of the polymer)×100%

Drug loading efficiency (%)=(weight of the loaded drug/total weight of the fed drug)×100%

Table 1 shows the calculation result above. It can be observed that the polymer PEG5k-b-PCDC2.8k nanoparticles have highly efficient encapsulation effect on the small molecule anticancer drug doxorubicin.

TABLE 1

The result of the drug loading content and drug loading efficiency in the doxorubicin-loading crosslinked micelle nanoparticles

| Polymer | Feeding ratio (wt. %) | Drug loading content (wt. %) | Drug loading efficiency (%) | Size (nm) | Particle size distribution |
|---|---|---|---|---|---|
| PEG5k-b-PCDC2.8k | 5 | 4.0 | 83.3 | 150.3 | 0.17 |
| | 10 | 7.4 | 80.0 | 162.1 | 0.22 |
| | 15 | 9.1 | 68.2 | 173.2 | 0.19 |

Figure 7:
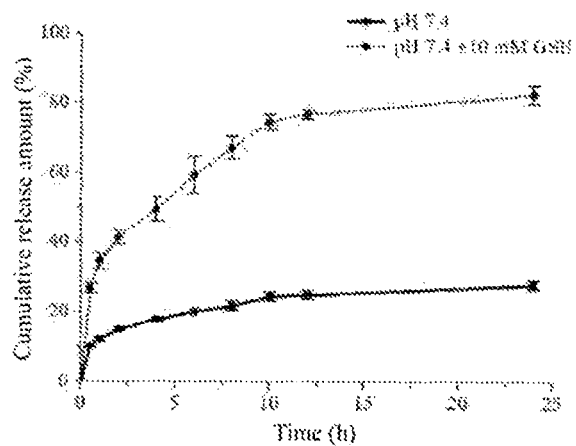
FIG. 7 is a graph showing the in vitro release result of the crosslinked nanoparticles of polymer PEG5k-b-PCDC2.8k which carry doxorubicin in Example 7.

The experiment of doxorubicin release was performed in a thermostatic shaker at 37° C. under 200 rpm shaking. The comparison of drug release was performed with two parallel groups, each group had duplicate samples. Group 1: crosslinked doxorubicin-loaded polymer nanoparticles were released in PB (10 mM, pH 7.4) which simulated the intracellular reducing environment through the addition of 10 mM glutathione (GSH); Group 2: the release of crosslinked doxorubicin-loaded polymer nanoparticles in PB (10 mM, pH 7.4); the concentration of the drug-loaded polymer nanoparticles was 25 mg/L; 0.5 mL of the solution was taken and put into a dialysis bag (MWCO: 12,000-14,000) for release, the corresponding solvents for dialysis (25 mL) were added to each tube. At the pre-determined time interval, 5.0 mL of the medium exterior the dialysis bag was taken out for the test, meanwhile 5.0 mL of the corresponding medium was supplemented into the tubes. The drug concentration in the solution was determined with EDINBURGH FLS920 fluorescence spectrophotometer. FIG. 7 shows the relationship between the cumulative release amount of doxorubicin and time. It can be observed from the figure that, after adding the reducing substance glutathione (GSH) which simulates the cancer cells, the release was significantly faster than the condition that GSH component was not added. It suggests that in the presence of 10 mM reducing substance GSH, the drug-loaded crosslinked nanoparticles are able to effectively release the drug.

Figure 8:
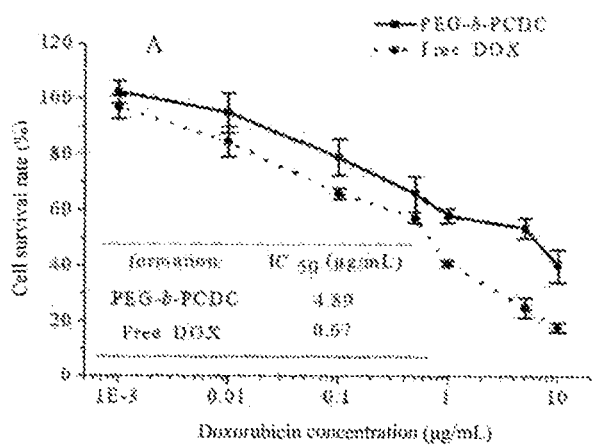
FIG. 8 is a graph showing the toxicity of the crosslinked nanoparticles of polymer PEG5k-b-PCDC2.8k which carry doxorubicin on Raw264.7 cells in Example 7.

The cytotoxicity of DOX-loaded PEG5k-b-PCDC2.8k crosslinked nanoparticles on Raw264.7cells, MCF-7 cells was tested with MTT method. The drug-carrying, non-crosslinked nanoparticles and the free drugs were used as control. As an example, the Raw264.7 cells ($1\times10^4$ cells/mL) were seeded into 96-well plate, 100 μL per well. The cells were cultured till they adhere to the culture vessels. Then for the experimental groups, the solutions which contained doxorubicin-loaded crosslinked nanoparticles at 0.01, 0.1, 1, 5, 10, 50 and 100 μg/mL, the solution of doxorubicin-loaded, non-crosslinked nanoparticles and fresh medium containing free doxorubicin were added respectively. In addition, cell-free control wells and medium-free blank wells were provided. The wells were provided in quadruplicate. After 48 h incubation in the incubator, the 96-well plates were taken out, then 10 μL MTT (5.0 mg/mL) was added thereto. After another 4 h incubation, 150 μL DMSO was added into each well to dissolve the crystal formed. The absorption value (A) at 492 nm was determined with microplate reader. A zero adjustment was performed with the medium-free blank wells. The cell survival rate was calculated. With reference to FIG. 8, it can be observed from the experimental result that, the median lethal concentration of doxorubicin-loaded crosslinked nanoparticles on Raw264.7 cells is 4.89 μg/mL. Therefore the DOX-carrying PEG5k-b-PCDC2.8k crosslinked nanoparticles can effectively release drugs in the cells and kill the cancer cells.

EXAMPLE 8

Determination of in vivo Blood Circulation of Drug-Loaded PEG5k-h-PCDC2.8k Crosslinked Nanoparticles in Mice C57BL/6 black mice with body weight of about 18||20 g, aged 4~6 weeks (The Experimental Animal Center, The Shanghai Institutes for Biological Sciences of the Chinese Academy of Sciences) were used in the experiment. The mice were weighed, equally grouped based on body weight. The drug-carrying nanoparticles and free drugs were injected into the mice via tail veins, where the dosage of DOX was 10 mg/kg. The blood samples (approximately 10 μL) were collected at time points of 0, 0.25, 0.5, 1, 2, 4, 8, 12 and 24 h. The exact weight of the blood was determined through weighing by difference method, then 100 μL Triton (concentration: 1%) and 500 μL DMF (which contained 20 mM DTT, 1 M HCl) were added. The sample was subjected to extraction, followed by centrifugation (20,000 rpm, 20 min). Then the supernatant was collected, the amount of DOX at each time point was determined through fluorescence.

Figure 9:
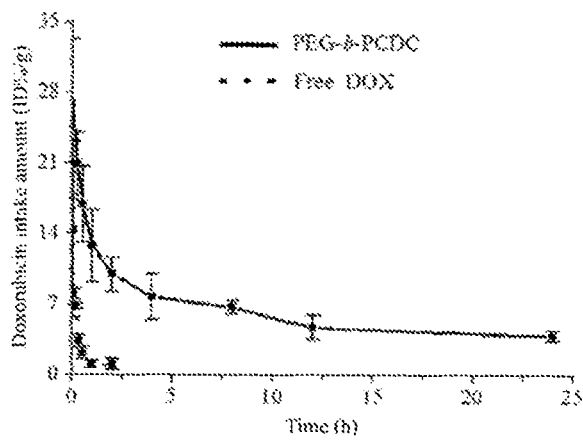
FIG. 9 is a graph showing the in vivo blood circulation of the doxorubicin-loaded polymer PEG5k-b-PCDC2.8k crosslinked nanoparticles in mice in Example 8.

FIG. 9 is a graph showing the in vivo blood circulation of the doxorubicin-loaded polymer PEG5k-b-PCDC2.8k crosslinked nanoparticles in mice. The horizontal axis represents time point, while the vertical axis presents the amount of DOX per gram blood against the total amount of injected DOX (ID %/g). It can be seen from the graph that the free DOX has a short circulation time; DOX can barely be determined after 2 h. However the drug-carrying crosslinked nanoparticles still have 4 ID %/g after 24 h. Thus its elimination half-life of the drug-carrying crosslinked nanoparticles in mice can be calculated as 4.67 hours, while the elimination half-life of free DOX is only 0.21 hours. Therefore the drug-carrying crosslinked nanoparticles are stable in the mice, have a relatively long circulation time.

EXAMPLE 21

The Biological Distribution of the Drug-Carrying PEG5k-b-PCDC2.8k Crosslinked Nanoparticles to the Melanoma-Bearing Mice C57BL/6 black mice with body weight of about 18~20 g, aged 4~6 weeks were used in the experiment; $1\times10^6$B16 melanoma cells were subcutaneously injected. After two weeks, when the size of the tumors was 100~200 mm$^3$, the drug-loaded nanoparticles and free DOX were injected into the mice through tail veins (the dosage of DOX was 10 mg/kg). After 6, 12 and 24 hours, the mice were euthanized. The tumor, and the heart, liver spleen, lung and kidney tissue were taken out, washed and weighed. Then 500 μL of 1% Triton was added, the samples were minced with a homogenizer, extracted after adding 900 μL DMF (which contained 20 mM DTT, 1M HCl). After centrifugation (20,000 rpm, 20 min), the supernatant was collected, the amount of DOX at each time point was determined through fluorescence.

Figure 10:
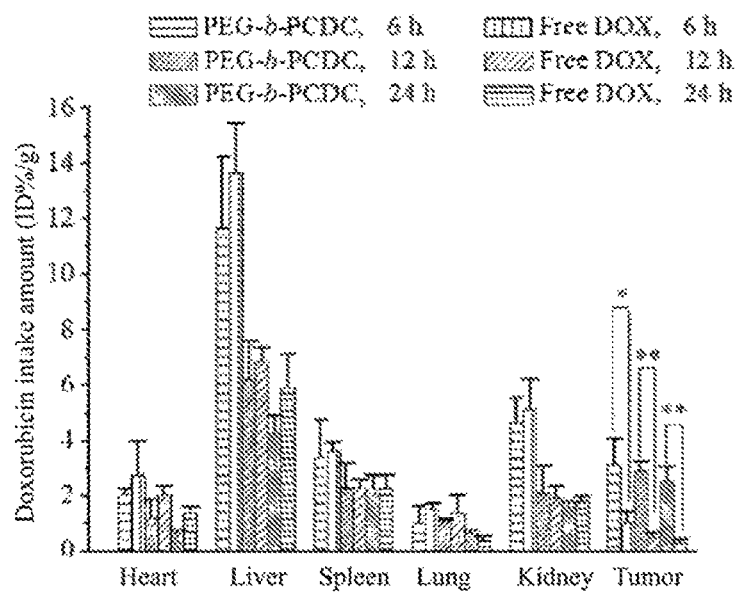
FIG. 10 is a graph showing the biological distribution of the doxorubicin-loaded polymer PEG5k-b-PCDC2.8k crosslinked nanoparticles to the melanoma-bearing mice in Example 9.

FIG. 10 is a graph showing the biological distribution result of the doxorubicin-loading polymer PEG5k-b-PCDC2.8k crosslinked nanoparticles to the melanoma-bearing mice. The horizontal axis represents tissue organ, while the vertical axis represents the amount of DOX per gram tumor or tissue against the total amount of injected DOX (ID %/g). The accumulation amounts of drug-carrying nanoparticles in tumor at 6, 12 and 24 h are 3.12, 2.93, 2.52 ID %/g respectively, which are 3~12 times larger than those of free DOX (1.05, 0.52 and 0.29 ID %/g respectively). It indicates that through EPR effect, the drug-loaded crosslinked nanoparticles accumulate more at the tumor sites, and may sustain for a longer time.

EXAMPLE 22

The Experiment of Treating Melanoma-Bearing Mice with Drug-Loaded PEG5k-b-PCDC2.8k Crosslinked Nanoparticles C57BL/6 black mice with body weight of about 18~20 g, aged 4~6 weeks were used in the experiment. The mice were weighed and equally grouped based on body weight, then $1\times10^6$ B16 melanoma cells were subcutaneously injected. After one week, when the size of the tumors was 30~50 mm$^3$, the drug-loaded nanoparticles and free DOX were injected into the mice through tail veins at Day 0, 2, 4, 6, and 8, where the amount of DOX in drug-carrying nanoparticles was 10, 20, 30 mg/kg, while the dosage of free DOX was 10 mg/kg. From Day 0 to 15, the body weight of the mice in each group was weighed every day. The size of the tumor was precisely measured with Vernier scale, where the method for calculating the volume of tumors was: V=(L×W×H)/2, (where L was the length of the tumor, W was the width of the tumor, H was the thickness of the tumor). The survival of the mice was observed continuously till the 46$^{th}$ day.

Figure 11:
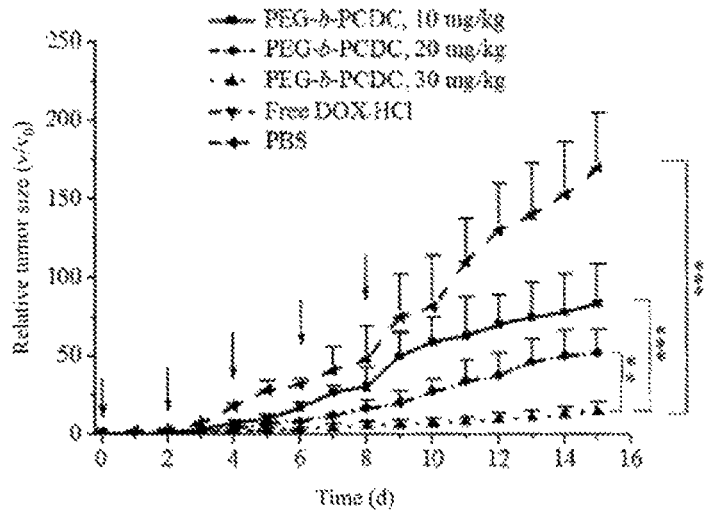
FIG. 11 is a curve graph showing that the doxorubicin-loaded polymer PEG5k-b-PCDC2.8k crosslinked nanoparticles inhibit tumor growth on melanoma-bearing mice in Example 10.
Figure 12:
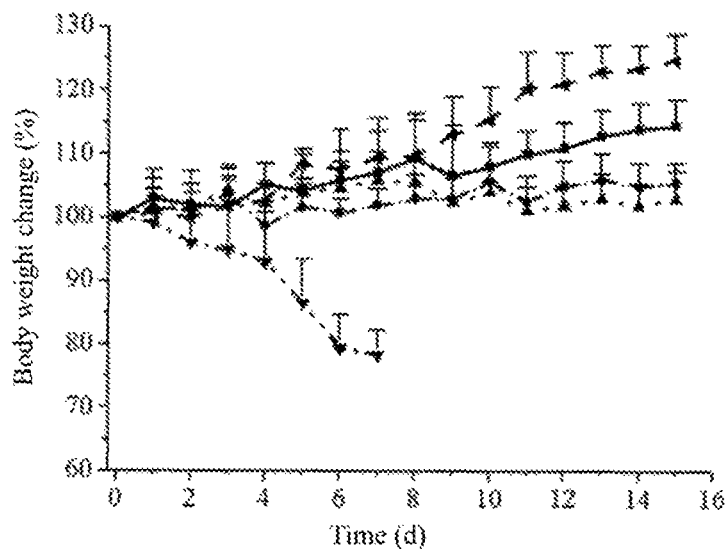
FIG. 12 is a curve graph showing the change of body weight of the mice in Example 10.
Figure 13:
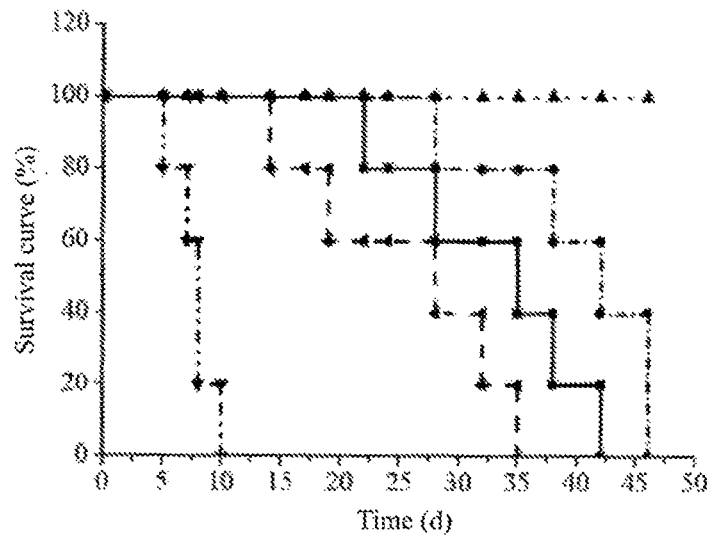
FIG. 13 is a curve graph showing the survival of the mice in Example 10.

FIG. 11 is a curve graph showing that the doxorubicin-loaded polymer PEG5k-b-PCDC2.8k crosslinked nanoparticles inhibit tumor growth on melanoma-bearing mice; FIG. 12 is a curve graph showing the change of body weight of the mice. FIG. 13 is a curve graph showing the survival of the mice. From the figures it can be observed that, at the DOX concentration of 30 mg/kg, after 16-day treatment with DOX-carrying nanoparticles, the tumors were obviously inhibited. However, though DOX may also inhibit tumor expansion, it had severe toxic side effect on the mice. Even though the DOX concentration in the drug-loaded nanoparticles reaches 30 mg/kg, the body weight of the mice was almost not changed, indicating that the drug-loaded nanoparticles had no toxic side effects on the mice. Meanwhile the body weight of the mice in DOX group decreased 23% in 7 days, indicating that DOX had severe side effects on the mice. Both at the DOX concentration of 30 mg/kg, in the group where the mice were treated with DOX-carrying nanoparticles for 46 days, all the mice survived, while the mice treated with DOX all died on the $10^{th}$ day of treatment; further, in the control group where PBS was given, all the mice died on the $35^{th}$ day. Therefore, the drug-loaded nanoparticles can effectively inhibit tumor growth, and have no toxic side effect on the mice; further, they can prolong the life of the tumor-bearing mice.

The results above indicate that the polymer prepared from the monomer of the present disclosure has favorable biocompatibility. When used as a drug carrier, it can increase the in vivo circulation time of the anti-cancer drugs, increase the accumulation ratio of the drug at the tumor site, and prevent the drug from damaging the normal tissue. It can effectively kill the tumor cells, meanwhile it has minimal effect on the normal cells.

The invention claimed is:

1. A cyclic carbonate monomer containing double-sulfur five-membered ring functional group, wherein the cyclic carbonate monomer containing double-sulfur five-membered ring functional group has following chemical structure:

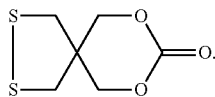 [SMILES: O=C1OCC2(CO1)CSSC2]

2. A method for preparing the cyclic carbonate monomer containing double-sulfur five-membered ring functional group of claim 1, wherein the method comprises the following steps: reacting dibromoneopentyl glycol with sodium hydrosulfide monohydrate in a polar solvent to obtain Compound A; then oxidizing the Compound A in air to obtain Compound B; finally in nitrogen atmosphere and a cyclic ether-based solvent, reacting the Compound B with ethyl chloroformate to obtain the cyclic carbonate monomer containing double-sulfur five-membered ring functional group.

3. The method for preparing the cyclic carbonate monomer containing double-sulfur five-membered ring functional group according to claim 2, wherein the molar ratio of dibromoneopentyl glycol to sodium hydrosulfide monohydrate is (2.5~10):1; the molar ratio of Compound B to ethyl chloroformate is 1:(2~4).

4. The method for preparing the cyclic carbonate monomer containing double-sulfur five-membered ring functional group according to claim 2, wherein for preparing the Compound A, the reaction temperature is 50° C., and the reaction time is 48 h; for preparing the Compound B, time for oxidizing the Compound A is 24 h; for preparing the cyclic carbonate monomer, the reaction temperature is maintained with ice water bath, and the reaction time is 4 h.

5. The method for preparing the cyclic carbonate monomer containing double-sulfur five-membered ring functional group according to claim 2, wherein the polar solvent is N,N-dimethylformide (DMF); the cyclic ether-based solvent is tetrahydrofuran or 1,4-dioxane.

6. The method for preparing the cyclic carbonate monomer containing double-sulfur five-membered ring functional group according to claim 2, wherein the Compound A is firstly dissolved in an ether-based solvent, then oxidized in air to obtain the Compound B.

7. The method for preparing the cyclic carbonate monomer containing double-sulfur five-membered ring functional group according to claim 6, wherein the ether-based solvent is tetrahydrofuran or 1,4-dioxane.

8. The method for preparing the cyclic carbonate monomer containing double-sulfur five-membered ring functional group according to claim 2, wherein the method further comprises a purification treatment as follows:
(1) purification of the Compound A: when the reaction is completed, the reaction mixture is subjected to distillation under reduced pressure for removing the solvent, then diluted with distilled water, extracted with ethyl acetate; finally the organic phase is evaporated with rotary evaporator, and the yellow and viscous Compound A is obtained;
(2) purification of the cyclic carbonate monomer containing double-sulfur five-membered ring functional group: filtration is performed after the reaction is completed; the filtrate is concentrated with a rotary evaporator, then recrystallized with ethyl ether to obtain a yellow crystal, which is the cyclic carbonate monomer containing double-sulfur five-membered ring functional group.

* * * * *